(12) United States Patent
Barrow

(10) Patent No.: US 8,015,677 B2
(45) Date of Patent: Sep. 13, 2011

(54) EMBALMING FLUID

(75) Inventor: Dermot Christopher John Barrow, East Sussex (GB)

(73) Assignee: AARD-BALM Limited, Essex (GB)

( * ) Notice: Subject to any disclaimer, the term of this patent is extended or adjusted under 35 U.S.C. 154(b) by 911 days.

(21) Appl. No.: 10/449,502

(22) Filed: Jun. 2, 2003

(65) Prior Publication Data

US 2003/0206884 A1 Nov. 6, 2003

Related U.S. Application Data

(63) Continuation-in-part of application No. PCT/GB01/05337, filed on Dec. 3, 2001, which is a continuation-in-part of application No. 09/809,433, filed on Mar. 16, 2001, now abandoned.

(30) Foreign Application Priority Data

Dec. 1, 2000 (GB) .................................. 0029410.8

(51) Int. Cl.
*A01N 1/00* (2006.01)

(52) U.S. Cl. .............................. 27/22.1; 27/22.2; 424/75

(58) Field of Classification Search .................. 27/22.1, 27/22.2; 424/75
See application file for complete search history.

(56) References Cited

U.S. PATENT DOCUMENTS

| | | | | |
|---|---|---|---|---|
| 1,870,123 A * | 8/1932 | Jones | ............................... | 424/75 |
| 2,880,134 A * | 3/1959 | Robinette | ...................... | 424/75 |
| 3,202,574 A * | 8/1965 | Berliner | .......................... | 424/75 |
| 3,912,809 A * | 10/1975 | Rendon | .......................... | 27/22.2 |
| 3,983,252 A | 9/1976 | Buchalter | | |
| 3,993,777 A * | 11/1976 | Caughman et al. | ........... | 514/642 |
| 4,048,336 A * | 9/1977 | Winicov et al. | ............... | 514/694 |
| 4,195,175 A * | 3/1980 | Peniston et al. | ................ | 536/20 |
| 4,296,130 A * | 10/1981 | Herschler | ...................... | 514/711 |
| 4,364,929 A * | 12/1982 | Sasmor et al. | ............. | 424/78.07 |
| 4,500,337 A * | 2/1985 | Young et al. | .................. | 504/151 |
| 4,591,610 A * | 5/1986 | Grollier | .......................... | 524/55 |
| 4,675,327 A * | 6/1987 | Fredrick | ....................... | 514/383 |
| 4,755,378 A | 7/1988 | Buxton et al. | | |
| 4,944,892 A * | 7/1990 | Leathers et al. | .............. | 510/199 |
| 4,946,669 A * | 8/1990 | Siegfried et al. | ........... | 435/40.52 |
| 5,622,695 A * | 4/1997 | Campbell et al. | ............... | 424/75 |
| 5,624,612 A * | 4/1997 | Sewall et al. | ................... | 264/4.1 |
| 5,629,024 A * | 5/1997 | Kessler et al. | ................. | 424/667 |
| 5,670,333 A | 9/1997 | Alldread et al. | | |
| 5,679,333 A * | 10/1997 | Dunphy | ........................... | 424/75 |
| 5,716,611 A * | 2/1998 | Oshlack et al. | ............. | 424/78.25 |
| 5,885,620 A * | 3/1999 | Foret | .............................. | 424/669 |
| 5,948,397 A * | 9/1999 | Van Kersen et al. | ............ | 424/75 |
| 5,967,202 A * | 10/1999 | Mullen et al. | .................. | 141/104 |
| 5,977,153 A * | 11/1999 | Camiener | ...................... | 514/392 |
| 5,998,483 A * | 12/1999 | Camiener | ...................... | 514/705 |
| 6,153,229 A | 11/2000 | Foret | | |
| 6,156,785 A * | 12/2000 | Stefansson et al. | ............ | 514/432 |
| 6,306,835 B1 * | 10/2001 | Daly et al. | ...................... | 514/55 |
| 6,391,294 B1 * | 5/2002 | Dettmar et al. | ............. | 424/78.11 |
| 6,482,942 B1 * | 11/2002 | Vittori | ............................ | 536/128 |
| 6,586,213 B2 * | 7/2003 | Kobzeff et al. | ............... | 435/104 |
| 6,601,275 B2 * | 8/2003 | Blake et al. | ..................... | 27/22.2 |

FOREIGN PATENT DOCUMENTS

JP 62063863 A * 3/1987
WO WO 00 18237 A 6/2000

OTHER PUBLICATIONS

Materials Handbook, pp. 7-8, 59-60, 172-175, 195, 189-190, 475, 271-273, 297-298, 402-404, 604-607, 665-666, 724-726, 859-860, 893-896.*
Materials Handbook, pp. 400 and 856-858.*
Merriam OnLine definition of "embalm".*

* cited by examiner

*Primary Examiner* — Leslie R Deak
*Assistant Examiner* — Benedict L Hanrahan
(74) *Attorney, Agent, or Firm* — Browdy and Neimark, PLLC

(57) ABSTRACT

An embalming fluid together with methods and kits for use in preparing the present embalming fluid, are provided, in which the fluid includes a pseudoplasticizing vegetable based, water-soluble polymer and a non-toxic disinfectant and which is essentially free from aldehyde. The preferred disinfectant is an iodine-based disinfectant, polyvinylpyrrolidone-iodine being particularly preferred.

27 Claims, No Drawings

EMBALMING FLUID

CROSS-REFERENCE TO RELATED APPLICATIONS

The present application is a continuation-in-part of copending parent application Ser. No. PCT/GB01/05337, filed Dec. 3, 2001, which in turn is a continuation in part of application Ser. No. 09/809,433, filed Mar. 16, 2001 now abandoned.

FIELD OF THE INVENTION

This invention relates to an embalming fluid for use in an embalming process.

BACKGROUND OF THE INVENTION

Embalming was developed and widely practised in ancient Egypt where, from around 6000 BC to 600 AD, as many as 400 million bodies are thought to have been mummified. The processes involved in traditional Egyptian embalming have led to the remarkable preservation of many bodies.

In more modern times in the USA, it was normal for bodies to be preserved by packing them in ice, a practice only changed at the time of the Civil War when national war cemeteries were established and the practice of arterial embalming became widespread for bodies to be transported to these cemeteries. Arterial embalming had become established in the United Kingdom in the $18^{th}$ century when bodies were first held for viewing. Demand grew and embalming became more established in the United Kingdom and particularly in the USA because of the distances involved in transporting bodies home.

The earliest modern embalming fluids contained arsenic but these fluids were soon replaced by formaldehyde based embalming fluids. Despite its unpleasant and dangerous properties, the use of formaldehyde in embalming has become almost universal.

Formaldehyde has long been used in the embalming profession as it confers excellent-preservative properties on the body and is an effective disinfectant and anti-microbial agent. Formaldehyde acts as a chemical fixing agent reacting with the soluble albumins (proteins) in the cells of the body and converting them to albuminoids, which are gels By pumping a formaldehyde solution through the vascular system of a body, the chemical agent perfuses into the tissues and exerts its disinfecting and preservative functions.

The modern embalming process involves flushing out the blood from the circulatory system of the body and replacing it with an embalming fluid which has a stabilising and protecting action on the body. The embalming fluid is injected into the arterial system of the cadaver and directly into some organs. Displaced body fluids are treated and disposed of via the public sewerage system or more usually by a contracted disposal firm.

The normal steps in the modern embalming process are as follows:

The body is placed in a proper position on the embalming table with the pubic area covered with a modesty cloth.
The body is washed and disinfected.
The face is shaved as necessary.
The eyes are closed. This is usually accomplished with a small curved plastic disc called an "eye cap" placed under the eyelid Perforations in the cap are sometimes present to help hold the eyelid in place.
The mouth is closed. This is usually accomplished by the placing of a specially designed "tack" in the upper and lower jaw. Each tack has a fine wire attached. By twisting the two wires together, the jaw is thus closed and the lips are set to the natural lip line using a cream to retain the proper position and to prevent dehydration.
The lower body orifice(s) may be plugged to prevent leakage.
The embalming solution is prepared. The modern embalming machine consists of a 2-3 gallon reservoir and an electric pump.
An incision is made over the carotid artery (where the neck meets the shoulder) or over the femoral artery (in the leg at the groin). The artery and a nearby vein are located and isolated.
A tube which is attached to the machine is inserted into the artery. A slightly larger tube is placed into the accompanying vein. This tube is attached via a hose to a collecting tank.
The fluid is injected into the artery under pressure by the embalming machine. As the blood is displaced by the fluid going in, it is forced out of the body from the vein and is disposed of. The pressure forces the embalming fluid into the capillaries and eventually to the cells of the body. After sufficient solution (typically approximately 2-10 liters depending on body size, more particularly vascular capacity) of solution are injected into the body, the blood has thinned the fluid coming through the vein tube is mostly embalming fluid.
The tubes are removed and the incision sutured.
The abdominal cavity is treated by the use of a hollow tube called a trocar that is used to aspirate gases and liquid contents under suction. A preservative chemical—and generally a more concentrated solution of the embalming fluid—is introduced via the trocar needle.
The body is again washed and cream is placed on the hands and face to prevent dehydration.
The hair is shampooed and the fingernails cleaned.
The body is covered with a sheet awaiting dressing and placement in the casket.
Cosmetics may be applied later to improve the natural colour of the body, although this will be less important if the embalming fluid includes a colorant. Much of the natural colour is created by blood in facial capillaries—this is no longer present after embalming. In the case of women, cosmetics used in life may also be used to recreate the "look" the person had during life. The hair is combed or set.

Formaldehyde is obtained commercially as an aqueous solution (formalin), which is usually a ca. 28% solution, and this is diluted down by the embalmer to ca. 1-3% concentration. Typically, and depending on body size, more particularly vascular capacity, 2-10 liters of diluted solution are used per embalming. A more highly concentrated form of solution is usually used as a cavity fluid.

Formaldehyde based embalming fluids may or may not contain other chemicals such as: colorants to redden or tan the body and give it a more life-like appearance, emollients to keep the skin soft and sequestrants to chelate divalent cations present in some tap waters, which may cause undesirable performance of the embalming fluid. Other additive chemicals can be disinfectants, humectants and pH stabilisers.

Although, formaldehyde is very effective in preserving tissues for the timescale required, it is nevertheless a very hazardous material and subjects the user to significant health risks. Studies have indicated the formaldehyde is a potential human carcinogen and airborne concentrations of above 0.1 part per million (ppm) can cause irritation of the eyes, nose and throat. The severity of the irritation increases as concentrations increase; at 100 ppm it is a danger to life and health. It has been linked to many different forms of cancer, nasal, lung, testicular and brain cancer as well as leukaemia. Studies conducted by the National Cancer Institute in the USA have shown that embalmers were at greater risk for leukaemia, testicular and brain cancer than the general public.

Within the last twenty five years the use of formaldehyde in the workplace has become subject to regulation. The US Department of Labour, occupational Safety and Health Administration (OSHA) has placed increasingly stringent limits upon formaldehyde vapour exposure in the workplace. The permissible exposure limit (PEL) is 0.75 ppm measured as an 8 hour time weighted average, it also specifies a 2 ppm short term exposure limit, (i.e. the maximum exposure allowed during a 15 minute period). Even with careful practice embalmers are often subject to high doses of formaldehyde during the embalming process. It has been determined that embalmers are exposed to formaldehyde at concentrations averaging up to 9 ppm during embalming. This is significantly higher than the allowable limits.

In addition, the disposal of formaldehyde can create problems as it should not enter sewerage systems or water courses. Its effect on soil and soil organisms is not known but formaldehyde has been shown to be toxic to fish and related species when introduced into water systems. Recommended disposal is via incineration.

There is therefore a long term problem both for the environment and for the embalmer himself in using formaldehyde in embalming fluids. Consequently there is a need for an embalming fluid which is essentially free from formaldehyde.

The awareness of the dangers associated with repetitive exposure to formaldehyde has provided a stimulus for a search for alternative embalming fluids. One replacement for formaldehyde is glutaraldehyde and the use of glutaraldehyde in embalming fluids is described in U.S. Pat. Nos. 5,405,606 and 5,607,668.

There have been other patents relating to formaldehyde-free embalming compositions. For example, U.S. Pat. No. 3,983,252 discloses a stable dialdehyde-containing disinfectant for use in the medical field and household objects. The compositions are described in this patent as being useful in leather tanning, tissue fixation in electric microscopy, as protein reactants and as embalming fluids.

U.S. Pat. No. 4,675,327 discloses an anti-microbial compositions for embalming preparations comprising a combination of a disinfectant and a plant growth-regulating compound. Disclosed as disinfectants are a wide variety of anti-bacterial agents such as sulfonamides, penicillin, cephalosporin and bactracin, and salts thereof. Disclosed as skin disinfectants are alcohols, sources of active halogens, phenolics and their derivatives, salts such as sodium hypochlorite, aldehydes including formaldehyde, peracids and their derivatives and quarternary ammonium compounds. Metal binding agents which are disclosed include compounds which can be chelating compounds, sequestering compounds or dyes. Other disinfectants disclosed are heavy metal disinfectants such as mercury compounds, copper compounds, silver compounds and arsenic compounds.

U.S. Pat. No. 5,670,333 discloses formaldehyde-free tissue preservative compositions useful in the field of mortuary science and histology. Disclosed in this patent is an aqueous solution of ethanol, ethanedial, a long chain polymer and a polar aprotic solvent as an arterial injection fluid for use in preserving animal bodies. Also disclosed as a formaldehyde-free composition are aqueous solutions of ethandedial, a polar aprotic solvent, a proteolytic enzyme, a surfactant, an antimicrobial agent and optionally a chelating agent, which composition is for use as a pre-injection composition to cleanse the circulatory system in preparation for the administration of the inventive tissue preservative composition. In addition, this patent describes a formaldehyde-free body cavity fluid for use in an embalming process which comprises an aqueous solution of ethanol, and organic compound, a polar aprotic solvent, ethanedial and bisphenol A.

U.S. Pat. No. 5,948,397 discloses skin care treatment for embalmed bodies. The goal of the composition disclosed in this patent is to prevent skin protein denaturing and desiccation of skin due to the process of embalming.

Aldehydes other than formaldehyde, especially glutaraldehyde have also found use in embalming. However, at least some of the above problems have also occurred here.

Accordingly, this invention aims to provide an essentially aldehyde-free embalming fluid that is non-toxic, easy to make up and use, effective, and which is also environmentally acceptable and biodegradable.

SUMMARY OF THE INVENTION

According to one aspect of the present invention, there is provided an embalming fluid essentially free of aldehyde, which fluid comprises:

(a) a water-soluble polymer able to and in amount sufficient to produce a pseudoplastic solution when dissolved in a predetermined amount of water;

(b) an effective amount of a non-toxic disinfectant, and (c) potable water in said predetermined amount, optionally with one or more additives selected from perfumes, colorants, sequestrants, anti-coagulants and humectants.

DETAILED DESCRIPTION OF EMBODIMENTS

A preferred embalming fluid embodying this invention comprises:

(a) 0.05-3% by weight of a vegetable based water-soluble polymer producing a pseudoplastic solution when dissolved in water;

(b) 0.05-2% by weight of a non-toxic disinfectant, and (c) portable water, the fluid optionally containing one or more additives selected from perfumes, colors, sequestrants, anti-coagulants and humectants.

The water can be tap water, demineralised water or deionised water.

Preferably the disinfectant/biocide is selected from iodine based compounds, preferably polyvinylpyrrolidone-iodine, chlorhexidine salts, hexachlorophene based compounds, cetrimide and triclosan.

Preferably the water soluble polymer is of vegetable origin, and is selected from seaweed based compounds, alginate based compounds (preferably sodium alginate), carrageenan based, cellulose based compounds, e.g. methyl cellulose hydroxypropyl) methyl cellulose, sodium carboxymethyl cellulose, hydroxyethyl cellulose, hydroxypropyl cellulose, microcrystalline cellulose, and plant based compounds e.g. guar gum, locust bean gum, acacia gum, gum tragacanth, karaya gum and plant bacteria based compounds e.g. xanthan gum. Preferred are alginates which are hydrophilic polysaccharides consisting of blocks of D-mannuronic acid linked in the β configuration through the 1- and 4-positions and L-guluronic acid units linked in the α configuration through the 1- and 4-positions.

The colorant is preferably carmine as this confers a realistic lifelike colour back to the skin.

The sequestrant is preferably selected from EDTA (ethylene diaminetetraacetic acid), phosphate salts (e.g. sodium hexametaphosphate, trisodium phosphate, tetrasodium phosphate, disodium hydrogen orthophosphate), citric acid salts (e.g. sodium citrate), carbonate salts (e.g. sodium carbonate).

The perfume is preferably a naturally based material, preferably a fragrant oil, e.g. rose oil (*Rosa centrifolium*), sandalwood oil (*Santalum album*) or geranium oil (*Pelargonium gravcolens*), which may be incorporated in dilute form. Other suitable fragrances include chrysanthemum oil and freesia oil.

An anti-coagulant is preferably added to aid penetration of the embalming fluid and to break down thickened blood areas. A preferred anti-coagulant is sodium citrate.

If a specific humectant is used it is preferably selected from glycerol, ethylene glycol, propylene glycol and sorbitol.

The composition can be stored and transported in concentrated form i.e. without little or no added water and in its concentrated form the fluid can be used a cavity fluid in the embalming process.

The invention also provides a method for embalming a dead body which method comprises administering into the body an aldehyde tree tissue preservative which comprises a fluid composition according to the first aspect of the invention, e.g. by draining blood from the circulatory system of a dead body and injecting the embalming fluid composition into the drained circulatory system and also into the major internal organs.

The components of the embalming fluid of this S invention will be combined in appropriate proportions according to the site into which the embalming fluid is to be injected. Conventionally, more concentrated solutions are injected into the major organs of the body, while more dilute solutions are injected into the vascular system.

Preferably, the ratio (by weight) of polymer to disinfectant is in the range from 10:1 to 0.5:1 when the polymer is a sodium alginate and the disinfectant is PVP-iodine with a weight ratio of about 1.8:1 being most preferred.

The foregoing sequence of steps is given for the purpose of illustration only and is not intended to be limiting on the invention. Embalming fluids in accordance with this invention will be administered in accordance with the professional judgement of the embalmer.

The embalming fluid used as an arterial injection fluid functions primarily as a tissue preservative, disinfecting and preserving body tissues, without the use of any aldehyde, in particular formaldehyde. It contains compounds within the composition that will clear clots and chelate divalent ions found in some tap waters. The thickener is pseudoplastic, thinning under shear allowing for easier introduction into the vascular system under slight positive pressure and also may impart some humectant properties which serves to draw moisture into the cells to help equilibration of cellular osmotic pressure. The thickener is a high molecular weight long chain polymer that tends to fill vacant intercellular spaces giving rigidity to the cellular structure.

A preferred composition of the embalming fluid of this invention comprises:

(a) an iodine disinfectant, preferably polyvinylpyrrolidone-iodine (known as Povidone-Iodine and/or PVP-Iodine). Polyvinylpyrrolidone is a non-ionic, non-detergent water soluble organic polymer that is characterised by an unusual complexing ability, by its colloidal properties and by its physiological inertness. Its iodine complex is a well known iodophor that is a highly effective germicide providing a broad spectrum of microbiocidal action against virtually all microbes. Iodine is the active disinfectant. The concentration of disinfectant in the composition is preferably 0.05-2% by weight and more preferably 0.051.5% by weight.

(b) a thickener which is preferably vegetable, e.g. seaweed based and more preferably sodium alginate. It has pseudoplastic properties, which make for ease of preparation and injection but gives some thickening when the force is removed. It also contributes some antiseptic properties. Other thickeners from the list detailed previously can also be used advantageously in a similar way. The concentration of thickener in the composition is about 0.05-3% by weight and preferably 0.1-2% by weight.

(c) a colorant added to give a more realistic skin colour to the cadaver. The preferred colorant is carmine extract at a concentration of preferably about 0.01-0.1% by weight.

(d) a sequestrant to prevent any interaction by high levels of divalent cations in the water used. The preferred sequestrant is sodium hexametaphosphate, which is an efficient sequestering agent and has the ability to sequester without appreciably altering the pH of the system and it also sequesters over a wide pH range. The concentration of sequestrant in the composition is about 0.1-1% by weight and preferably 0.1-0.5% by weight.

(e) a perfume, naturally based and preferably rose oil. The concentration of perfume in the composition is about 0.001-1% by weight and preferably 0.001-0.05% by weight.

(f) an anti-coagulant is preferably added to aid penetration of the embalming fluid and to break down thickened blood areas. The anti-coagulant is preferably sodium citrate. The concentration of anti-coagulant in the composition is about 0.01-0.7% by weight and preferably 0.01-0.03% by weight.

(g) the balance of the composition is water in an amount to constitute from 95.9 to 99.3% by weight of the embalming fluid.

(h) if a humectant is incorporated, then the preferred choice is propylene glycol with a preferred concentration of about 0.4% by weight.

The major organs of the body will usually be injected with a more concentrated solution, typically 2-4 times the concentration of that used for the vascular system; the limiting concentration of solution is determined by the viscosity of the embalming fluid.

A typical concentrated solution to be diluted before use as an embalming solution embodying this invention comprises 0.1-3% by weight of a vegetable-based polymer; 0.1-3% by weight of a preferably iodine-based disinfectant; 0.01-0.2% by weight of a perfume; 0.01-0.5% by weight of a colorant; 0.1-2% of sequestrant and 0.01-0.5% by weight of anti-coagulant; the balance being potable water.

A preferred method of making-up an embalming fluid using such a concentrated solution will now be described. 1 liter of the concentrated solution is poured into 7-10 liters of potable water in a suitable container and the whole is stirred with the minimum of stirring until a homogenous embalming fluid is obtained.

If using a powder mix, then a small portion, say 10%, of the potable water to be used is taken and a powder mix of the other components of the embalming fluid is sprinkled slowly into it. The mixture is stirred vigorously until the powder is well dispersed. The mixture is allowed to stand until all the powder has been taken up by the water and the resulting product is then added to the final quantity of the water and the whole mixture stirred until a homogenous solution is obtained. Stirring is discontinued and the solution is left to stand to equilibrate to ambient conditions.

The embalming fluid of this invention is a generally natural products-based composition; it is odourless and non-toxic. It can be used without risk of irritation to skin, mouth and nasal passages. It obviates the need for excessive air changes in the embalming room.

The embalming fluid has proved successful in the treatment and preparation of cadavers prior to a funeral. Natural skin colours can be maintained and there were no unpleasant odours present.

No deterioration of the cadaver was recorded over a 7 day period (average).

Cadavers have been held for up to 7 days under refrigeration conditions without deterioration. It is estimated that under refrigeration, very extended periods would prove to present few problems. Tests were also carried out with no refrigeration for a period of 21 days after treatment. After 18 days some leakage was noted from the rectum but no packing had been used under the test conditions. The body began to deteriorate after this time period but not too seriously. Barometric pressure at this period was unusually low, with thunder, the ambient temperature being 12-14° C.

The invention will be illustrated in a nonlimiting manner by the following Examples.

EXAMPLE 1

The body of a 53-year old Caucasian female weighing 140 lbs (64 kg) was embalmed using an embalming fluid in accordance with this invention. The embalming process took place five days after the woman had died from carcinomatosis, the cadaver having been refrigerated at +2° C. during this time. Rigor mortis had abated and the body was easily manoeuvrable when the embalming took place.

The embalming fluid consisted of a solution in water of the following ingredients:
1: Protanol GP 9356—(FMC Biopolymer);
2: PVP-iodine—(Graymor Chemical Hamburg GmbH);
3: Rose oil—(Elixarome Limited; and
4: Carmine—(Cybercolors Ltd.).
5: Sodium hexametaphosphate—(Rhodia Consumer Specialities)
6: Sodium citrate—(ADM Ingredients Ltd.)

The relative proportions of these ingredients, by weight, was 1:2:3:4:5:6=0.35:0.2:0.008:0.02:0.14: 0.013. These proportions may otherwise be expressed as 1:2:3:4:5:6=1:0.57: 0.023:0.057:0.4:0:0.037.

The major proportion of the fluid used was made up with water to give a solution having 1 part by weight of the above ingredients and 99 parts by weight water. A smaller amount of solution at twice this concentration (2 parts by weight of the above ingredients and 98 parts by weight water) can also be used for the major organs.

The body was washed prior to the embalming process and lower orifice plugging took place using an absorbent pad which had been immersed in the embalming fluid.

2 liters of the normal concentration embalming fluid were pumped into the vascular system of the cadaver, after which time the venous effusion was composed of embalming fluid rather than blood. 0.3 liters of the more concentrated fluid was then injected by means of a trocar into the abdominal cavity. The total quantity of fluid injected was thus 2.3 liters.

During the embalming process, the embalmer was wearing surgical (latex) gloves instead-of the heavy, protective type needed when an embalming fluid based on formaldehyde is used. This permits greater dexterity and hence allows the embalming to proceed more readily.

Immediately after the embalming process had been completed, the cadaver had a natural skin tone and showed no signs of discoloration. There was no unpleasant odour.

The cadaver was kept at a temperature of 7° C. for a period of seven days after which the skin tone was still natural in appearance, and the skin retained its suppleness. There was no evidence of discoloration or of deterioration of the tissue. There was still no unpleasant odour (a mild floral fragrance was evident), and no evidence of seepage of fluids from the body.

EXAMPLE 2

The body of an elderly male, approximately 80 years old, of average build and 6 ft. tall, was embalmed using an embalming fluid as described in Example 1 above. The embalming took place four days after death, by which time rigor mortis had abated and hypostasis was evident in the left side of the face, the left arm and hand. Both legs were slightly oedematous and the eyes were very sunken. The site chosen for injection of the embalming fluid was the right common carotid artery.

After one liter of fluid had been injected, it was apparent that the fluid was distributing around the body. Hypostasis was starting to clear and the face in particular the lips and eyeballs—was filling out to a natural condition.

After 4 liters had been injected, drainage by the "heart tap" method was commenced, the trocar needle entering the right atrium. Abdominal drainage was also carried out, after which 1 liter of the more concentrated embalming solution was injected into the abdominal cavity.

At the end of the embalming process, the cadaver presented a relatively natural appearance, with arms, trunk and legs assuming a relatively natural colour. There was no oedema in the legs. The hands were soft and pliable. The face still had some mottled marks, but these were clearing, and the eyes and mouth had a full, natural appearance.

The cadaver was stored for five days prior to burial After this period, there was no evidence of deterioration, either in terms of appearance or of odour There was no bruising or discoloration of the tissues. The face, including the eyes, ears and lips, had a natural pink colour which was not evident prior to embalming.

The invention claimed is:

1. A pseudoplastic embalming fluid essentially free of aldehyde, which embalming fluid comprises:
    (a) a vegetable based water-soluble polymer able to and in amount sufficient to produce a pseudoplastic solution when dissolved in a predetermined amount of water, of said water-soluble polymer being in amount of 0.05-3% by weight based on the weight of said embalming fluid whereby the embalming fluid thins under shear whereby injection into the vascular system under slight positive pressure is eased;
    (b) an effective amount of a non-toxic disinfectant, said effective amount being 0.05-2% by weight of based on the weight of said embalming fluid; and
    the balance of said embalming fluid being
    (c) potable water in said predetermined amount, and optionally one or more additives selected from perfumes, colorants, sequestrants, anti-coagulants and humectants.

2. The embalming fluid as claimed in claim 1 in which the water soluble polymer is selected from the group consisting of seaweed based polymer compounds, cellulose based polymer compounds, plant based polymer compounds and plant bacteria based polymer compounds.

3. The embalming fluid as claimed in claim 2 in which a said seaweed based polymer compound is selected from the group consisting of alginate based and carrageenan based water soluble polymers.

4. The embalming fluid as claimed in claim 2 in which a said cellulose based polymer compound is selected from the group consisting of methyl cellulose, hydroxypropyl methyl cellulose, sodium carboxymethyl cellulose, hydroxyethyl cellulose, hydroxypropyl cellulose and microcrystalline cellulose.

5. The embalming fluid as claimed in claim 2, in which a said plant or plant bacteria based polymer compound is selected from the group consisting of guar gum, locust bean gum, acacia gum, gum tragacanth, karaya gum and xanthan gum.

6. The embalming fluid as claimed in claim 1, in which said water soluble polymer is present in an amount 0.1-2% by weight of the fluid.

7. The embalming fluid as claimed in claim 1 in which said disinfectant is selected from the group consisting of iodine based compounds, hexachlorophene based compounds, cetrimide and triclosan.

8. The embalming fluid as claimed in claim 7, in which said disinfectant is polyvinylpyrrolidone-iodine.

9. The embalming fluid as claimed in claim 1, which contains a said colorant, the colorant being carmine-based.

10. The embalming fluid as claimed in claim 9, in which the colorant is present in an amount of 0.01-0.1% by weight of the fluid.

11. The embalming fluid as claimed in claim 1, in which a said sequestrant is present and is selected from the group consisting of citric acid salts and carbonate salts.

12. The embalming fluid as claimed in claim 1, in which a sequestrant is present and wherein the sequestrant removes any divalent salts from the embalming fluid and wherein the sequestrant is a phosphate salt selected from the group consisting of sodium hexametaphosphate, trisodium phosphate, tetrasodium phosphate and disodium hydrogen orthophosphate.

13. The embalming fluid as claimed in claim 11, in which the citric acid salt is sodium citrate and the carbonate salt is sodium carbonate.

14. The embalming fluid as claimed in claim 11, in which the sequestrant is present in an amount of 0.1-1% by weight of the fluid.

15. The embalming fluid as claimed in claim 14, in which the sequestrant is present in an amount of 0.1-0.5% by weight of the fluid.

16. The embalming fluid as claimed in claim 1, in which a said perfume is present and is selected from the group consisting of rose oil, sandalwood oil, geranium oil, chrysanthemum oil and freesia oil.

17. The embalming fluid as claimed in claim 16, in which the perfume is present in an amount of 0.001-1% by weight of the fluid.

18. The embalming fluid as claimed in claim 17 in which the perfume is present in an amount of 0.001-0.05% by weight of the fluid.

19. The embalming fluid as claimed in claim 1, which an anti-coagulant is present and said anti-coagulant is sodium citrate.

20. The embalming fluid as claimed in claim 19 in which the anti-coagulant is present in an amount of 0.01-0.7% by weight of the fluid.

21. The embalming fluid as claimed in claim 20, in which the anti-coagulant is present in an amount of 0.01-0.03% by weight of the fluid.

22. The embalming fluid as claimed in claim 1 in which a humectant is present and said humectant is selected from glycerol, ethylene glycol, propylene glycol and sorbitol.

23. The embalming fluid as claimed in claim 22 in which the humectant is present in an amount of 0.4% by weight of the fluid.

24. The embalming fluid as claimed in claim 1 which comprises 95.9% to 99.3% by weight potable water based on the weight of the embalming fluid.

25. The embalming fluid as claimed in claim 1 in which the water is selected from the group consisting of tap water, demineralised water and deionised water.

26. The embalming fluid as claimed in claim 1 in which the weight ratio of said vegetable based water-soluble polymer to said non-toxic disinfectant is in the range from 10:1 to 0.5:1 when the polymer is sodium alginate and the disinfectant is pvp-iodine.

27. The embalming fluid of claim 26 wherein said weight ratio is about 1.8:1.

* * * * *